US00PP28475P2

(12) United States Plant Patent
Ault

(10) Patent No.: US PP28,475 P2
(45) Date of Patent: Oct. 3, 2017

(54) ***VERNONIA* PLANT NAMED 'SUMMER'S SURRENDER'**

(50) Latin Name: ***Vernonia* hybrid**
Varietal Denomination: Summer's Surrender

(71) Applicant: James Robert Ault, Libertyville, IL (US)

(72) Inventor: James Robert Ault, Libertyville, IL (US)

(73) Assignee: CHICAGOLAND GROWS, INC, Glencoe, IL (US)

( * ) Notice: Subject to any disclaimer, the term of this patent is extended or adjusted under 35 U.S.C. 154(b) by 21 days.

(21) Appl. No.: 14/998,968

(22) Filed: Mar. 10, 2016

(51) Int. Cl.
*A01H 5/02* (2006.01)

(52) U.S. Cl.
USPC ..... Plt./263.1

(58) Field of Classification Search
USPC ..... Plt./263.1
See application file for complete search history.

*Primary Examiner* — June Hwu
(74) *Attorney, Agent, or Firm* — Penny J. Aguirre

(57) ABSTRACT

A new cultivar of *Vernonia* plant, 'Summer's Surrender', that is characterized by its bushy upright plant habit with stems that do not lodge, its plant habit that is distinctly more wide than tall, its foliage that is darker green in color, its resistance to rust and powdery mildew, in being reliably hardy in U.S.D.A. Zones 4 to 9 and in being very drought tolerant.

2 Drawing Sheets

Botanical classification: *Vernonia* hybrid.
Variety denomination: 'Summer's Surrender'.

BACKGROUND OF THE INVENTION

The present invention relates to a new and distinct cultivar of *Vernonia* plant of hybrid origin and will be referred to hereinafter by its cultivar name, 'Summer's Surrender'. The new cultivar represents a new herbaceous perennial grown for landscape use.

The new invention arose from an ongoing breeding program by the Inventor in Glencoe, Ill. The objectives of the breeding program are to develop improved cultivars of interspecific hybrids of *Vernonia* with novel ornamental traits such as plant habit, disease resistance, hardiness in U.S.D.A. Zone 5 and in ground cultural adaptability.

'Summer's Surrender' was derived from a cross made in September of 2010 under controlled conditions between unnamed unpatented plants of *Vernonia lettermannii* as the female seed parent and an unnamed and unpatented plant of *Vernonia arkansana* as the male pollen parent. 'Summer's Surrender' was selected in September of 2013 as a single unique plant amongst the resulting seedlings.

Asexual propagation of the new cultivar was first accomplished by shoot tip cuttings by the Inventor in June 2013 in Glencoe, Ill. Asexual propagation by shoot tip cuttings has determined that the characteristics of this cultivar are stable and reproduced true to type in successive generations.

SUMMARY OF THE INVENTION

The following traits have been repeatedly observed and represent the characteristics of the new cultivar. These attributes in combination distinguish 'Summer's Surrender' as a new and unique cultivar of *Vernonia*.

1. 'Summer's Surrender' exhibits a bushy upright plant habit with stems that do not lodge.
2. 'Summer's Surrender' exhibits a plant habit that is distinctly more wide than tall.

3. 'Summer's Surrender' exhibits foliage that is darker green in color.
4. 'Summer's Surrender' exhibits resistance to rust and powdery mildew.
5. 'Summer's Surrender' is reliably hardy in U.S.D.A. Zones 4 to 9.
6. 'Summer's Surrender' is very drought tolerant.

The female parent, an unnamed plant of *Vernonia lettermannii*, differs from 'Summer's Surrender' in having a plant size that is smaller in height and width, in having stems that have shown lodging and in having fewer florets per capitulum. The male parent, *Vernonia arkansana*, differs from 'Summer's Surrender' in having phyllaries that are shorter in length with long tapered tips that are incurved and held away from the capitulum base, in having more florets per capitulum, in having susceptibility to rust and in having leaves that are longer and wider in measurement and are densely covered with pubescence across the abaxial surfaces. 'Summer's Surrender' can also be compared to the cultivar *Vernonia lettermannii* 'Iron Butterfly' (not patented) and *Vernonia* 'Southern Cross' (not patented). 'Iron Butterfly' is similar to 'Summer's Surrender' in having a bushy, broad plant habit, in having stems that do not lodge and in having a high resistance to powdery mildew and rust. 'Iron Butterfly' differs from 'Summer's Surrender' in having fewer florets per capitulum, in having leaves that are smaller in size with margins that are entire and in having a plant size that is smaller in height and width. 'Southern Cross' is similar to 'Summer's Surrender' in having a similar leaf shape, margins and size and in having the same resistance to lodging. 'Southern Cross' differs from 'Summer's Surrender' in having a plant habit that is more narrow in shape, in having a plant size that is smaller in height and width, in being susceptible to rust and in producing fewer florets per capitulum.

BRIEF DESCRIPTION OF THE DRAWINGS

The accompanying colored photographs illustrate the overall appearance and distinct characteristics of the new

*Vernonia*. The photographs were taken of 'Summer's Surrender' as grown in a trial garden in Glencoe, Ill.

Figure 1:
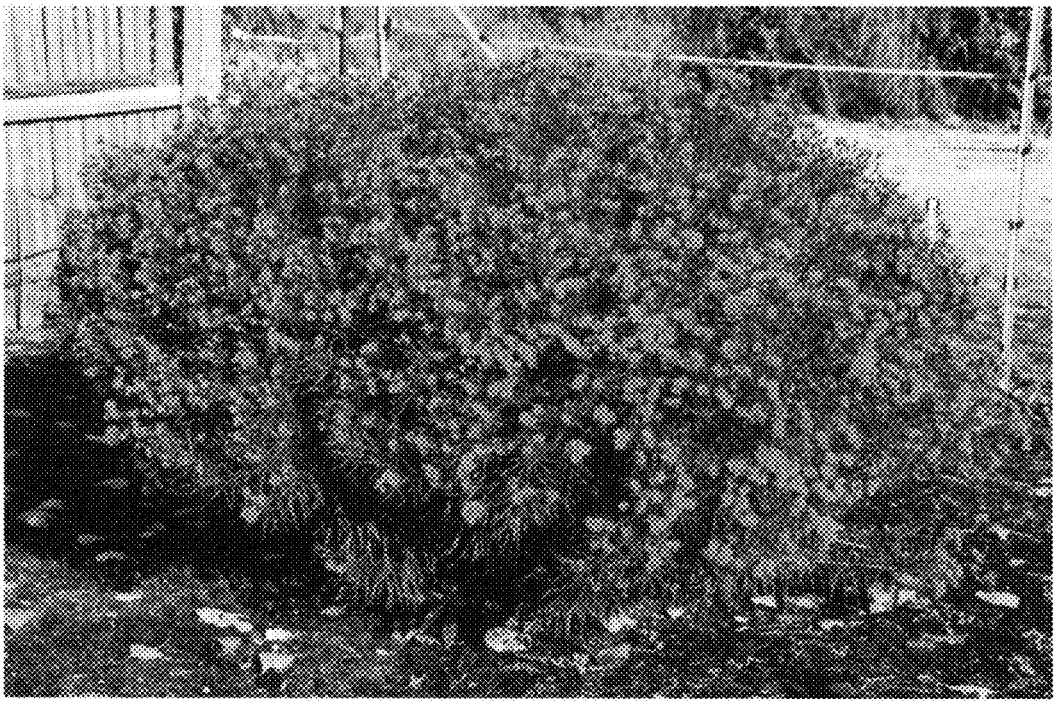

The photograph in FIG. 1 provides a top view of a 3 year-old plant of 'Summer's Surrender' in bloom.

Figure 2:
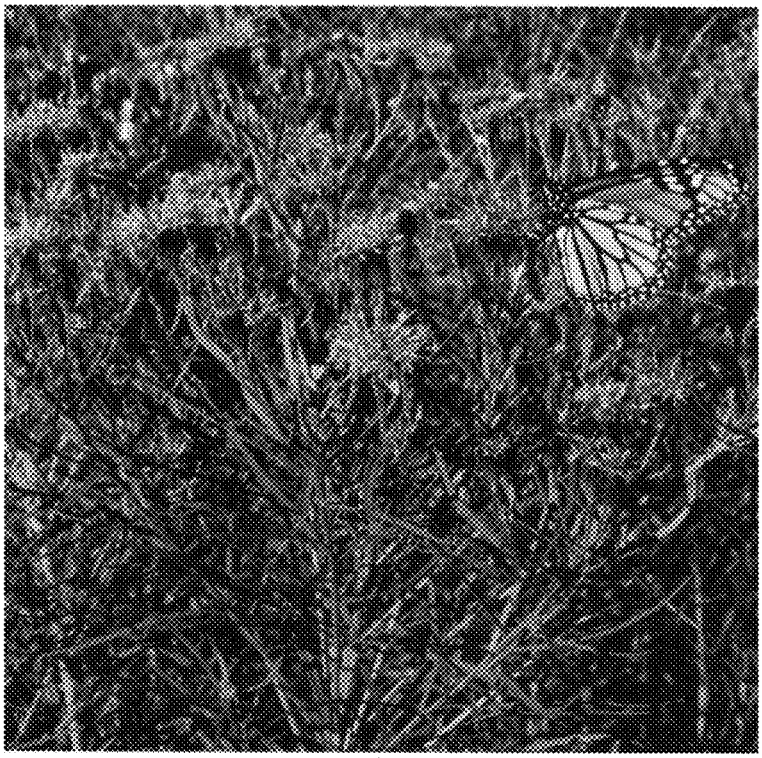

The photograph in FIG. 2 provides a close up view of the foliage and flowers of a 5 year-old plant of 'Summer's Surrender'.

Figure 3:
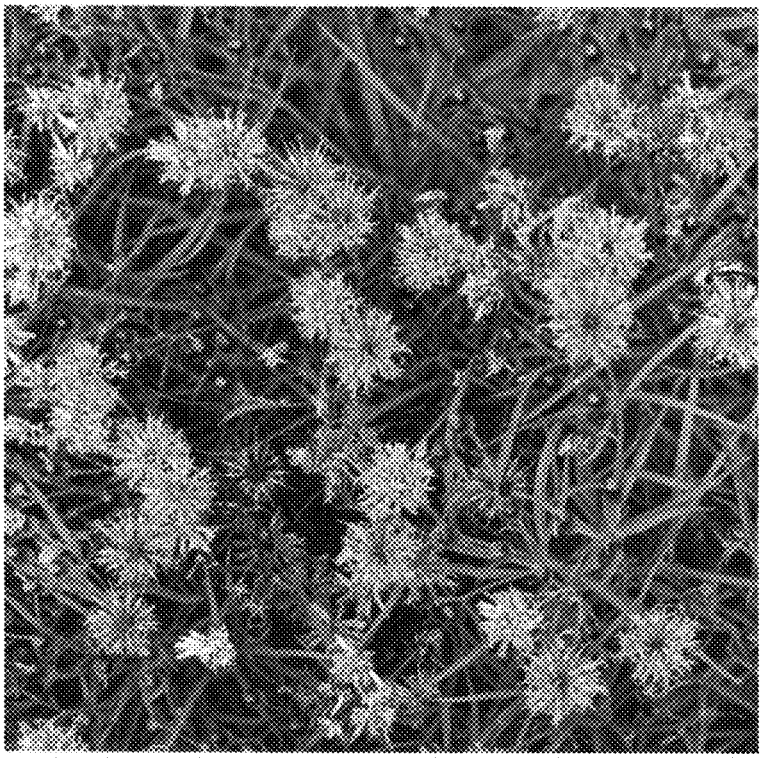

The photograph in FIG. 3 provides a close up view of the foliage and flowers of a 3 year-old plant of 'Summer's Surrender'.

The colors in the photographs are as close as possible with the photographic and printing technology utilized and the color values cited in the Detailed Botanical Description accurately describe the colors of the new *Vernonia*.

DETAILED BOTANICAL DESCRIPTION

The following is a detailed description of three year-old plants of the new cultivar as grown outdoors in a trial plot in Glencoe, Ill. The phenotype of the new cultivar may vary with variations in environmental, climatic, and cultural conditions, as it has not been tested under all possible environmental conditions. The color determination is in accordance with The 2015 R.H.S. Colour Chart of The Royal Horticultural Society, London, England, except where general color terms of ordinary dictionary significance are used.

General description:

*Blooming period.*—Four to five weeks from early September to early October in northern Illinois.

*Plant type.*—Herbaceous Perennial.

*Plant habit.*—Bushy upright plant habit with stems that do not lodge.

*Height and spread.*—In-ground trial plants 3 years in age; 123 cm in height and 210 cm in width at peak bloom, in-ground trial plants 5 years in age; 125 cm in height and 190 cm in width at peak bloom.

*Hardiness.*—At least hardy in U.S.D.A. Zone 4 to 9.

*Diseases.*—Highly resistant to powdery mildew and rust.

*Root description.*—Fibrous, 155A in color.

*Propagation.*—Shoot tip cuttings.

*Growth rate.*—Vigorous.

*Root development.*—Shoot tip cuttings will root under mist in 4 to 5 weeks in late spring to early summer, rooted cutting will fully root in a 2.5 inch pot in about two months and when transplanted in fall and overwintered in a 4.5 inch pot, they will bloom the following spring.

Stem description:

*Shape.*—Main branch; round, lateral branches oval to round.

*Stem color.*—Main branch; a blend of 145A, 141A and 144D, leaf scars 200A, lateral branches; a blend of 145A, 141A and 144D.

*Stem size.*—Main branches; average of 99.5 cm in length and an average of 5 mm in diameter, lateral branches; average of 15 cm in length and an average of 2 mm in width.

*Stem surface.*—Glossy, smooth and ridged, leaf scars are present and an average of 2 scars per linear cm.

*Branching number.*—An average of 120 main branches, an average of 15 lateral branches per main branch.

*Branching habit.*—Main branches occur from the base held at straight upright vertical angle, lateral branches held at a 65° angle (90°=vertical), very strong.

Foliage description:

*Leaf division.*—Simple.

*Leaf arrangement.*—Alternate, sometimes opposite.

*Leaf shape.*—Linear.

*Leaf size.*—Up to 12 cm in length and 4 mm in width.

*Leaf number.*—Average of 75 per main branch and 21 per lateral branch.

*Leaf base.*—Acute.

*Leaf apex.*—Acute.

*Leaf margin.*—Finely denticulate, teeth spread an average of 4 mm apart and color of teeth is 151A in color, the entire space between matches leaf color.

*Leaf venation.*—Pinnate, one main middle vein, upper and lower surface color; base of vein to a quarter up is N144A, remaining vein to tip matches leaf color.

*Leaf surface.*—Both surfaces glabrous and dull.

*Internode length.*—Main branch up to 2 cm, lateral branches up to 4 cm.

*Leaf color.*—Young and mature upper and lower surfaces; 146A.

*Leaf attachment.*—Sessile.

*Petioles.*—No petioles, leaves growing directly from the stem, also growing underneath lateral branches.

Inflorescence description:

*Inflorescence type.*—Corymb.

*Inflorescence number.*—1 per stem.

*Inflorescence fragrance.*—None.

*Inflorescence size.*—Average of 30 cm in depth and 28 cm in diameter.

*Peduncles.*—Oval in shape, up to 3 cm in length and 2 mm in diameter, surface is dull, ridged and glabrous, color is a blend of 145A, 141A and 144D.

*Pedicels.*—Oval in shape and up to 2 cm in length and 1 mm in diameter, surface is dull, ridged and glabrous, color is a blend of 145A, 141A and 144D.

*Phyllaries.*—About 50 per capitulum, discoid head, acute tips, entire margins, bluntly acute base, smaller phyllaries linear in shape, up to 3 mm in length and 1 mm in width, color of outer and inner surfaces; tip is N92A, remaining surfaces 144A in color, larger phyllaries lanceolate in shape average of 7 mm in length and 1 mm in width, color of outer and inner surfaces; tip to mid section and margins a blend of 59A and 60B, mid section to base 196A.

*Floret buds.*—Linear in shape, average of 5 mm in length and 1 mm in width, color; base 155A, mid section a blend of N82C and N80A, tip 79A.

*Flower longevity.*—Average of 3 to 5 days per floret, depending on temperature.

*Floret type.*—Discoid florets, no ray florets.

*Floret quantity.*—Average of 28 per capitulum.

*Floret.*—Just before floral anthesis; 1 cm in depth, 5 mm in width, elongated tube in shape and flat on top, base a blend of 138A, and 146A, mid section a blend of 138A and N92A, tip is a blend of N92A and 158A, when open; average of 1 cm in diameter and 1.5 cm in depth, base a blend of 143A and 142B, mid section a blend of N92A, and N79A, tip is a blend of N81A, 164B, 165A, N187A and NN155A.

*Petals.*—5 petals, 50% of petals fused, free top portion; base to mid section is linear in shape, un-fused portion of petals drop into downward and inward hanging angles and slightly curl under, tube is 5 mm in length and 1 mm in width, loose petals at top are 3 mm in length and 0.5 mm in width, petal tips acute in shape, inner and outer surfaces are glabrous and slightly velvety, entire margins, base fused to tube, color; inner and outer surfaces; base and mid section 83B, tips 83A.

*Pistils.*—1 per floret, bi-fid stigma, 86A in color, 2 mm in length and 3 mm in width, style 1 cm in length and <0.5 mm in width, a blend of 86A and NN155B in color, ovary is 2 mm in length and 1 mm in width and oval in shape, NN155A in color, pappus bristles at base, 6 mm in length, color ranging between NN155A and 86C.

*Stamens.*—1 per floret, 4 filaments very fine, 5 mm in length, translucent, close to NN155B in color, 2 anthers, 4 mm in length and 2 mm in width, NN155A, tip 86A, moderate amount of pollen observed when first blooming; NN155A in color.

*Fruit/seeds.*—Fruit and seed production was not observed to date.

It is claimed:

1. A new and distinct variety of *Vernonia* plant designated 'Summer's Surrender' as described and illustrated herein.

* * * * *